(12) United States Patent
Maguire, Jr. et al.

(10) Patent No.: US 8,065,772 B2
(45) Date of Patent: Nov. 29, 2011

(54) SCRUBBING ELEMENT WITH WELDED WIRE LEADER

(75) Inventors: Walter L. Maguire, Jr., Guilford, CT (US); Shaun Sweeney, Hamburg, NJ (US)

(73) Assignee: Cygnus Medical, LLC, Branford, CT (US)

( * ) Notice: Subject to any disclaimer, the term of this patent is extended or adjusted under 35 U.S.C. 154(b) by 599 days.

(21) Appl. No.: 11/414,284

(22) Filed: Apr. 28, 2006

(65) Prior Publication Data

US 2006/0191087 A1 Aug. 31, 2006

Related U.S. Application Data (63) Continuation-in-part of application No. 10/403,133, filed on Mar. 31, 2003, now abandoned.

(51) Int. Cl.
*B08B 9/04* (2006.01)

(52) U.S. Cl. ............ 15/104.2; 134/6; 134/22.11; 134/8; 15/104.05; 15/104.16; 15/164

(58) Field of Classification Search .................. 134/6, 8, 134/22.1, 22.11, 22.12, 22.13; 15/104.05, 15/104.16, 160, 164, 168, 206, 104.2
See application file for complete search history.

(56) References Cited

U.S. PATENT DOCUMENTS

| 4,733,425 | A | 3/1988 | Hartel et al. ..................... 15/206 |
| 4,867,797 | A | 9/1989 | Thomasen et al. .............. 134/18 |
| 4,887,622 | A | 12/1989 | Gueret .......................... 132/320 |
| 5,489,531 | A | 2/1996 | Benson ......................... 435/264 |
| 5,615,439 | A | 4/1997 | Bourrelly ..................... 15/104.2 |
| 6,224,544 | B1 | 5/2001 | Takada .......................... 600/155 |
| 6,481,445 | B1 | 11/2002 | Miraglia ....................... 132/218 |
| 2001/0016962 | A1* | 8/2001 | Moore et al. ............... 15/104.16 |

* cited by examiner

*Primary Examiner* — Alexander Markoff
(74) *Attorney, Agent, or Firm* — St. Onge Steward Johnston & Reens LLC (57) ABSTRACT

A cleaning element for lumen of surgical instruments includes a brush and a flexible metal leader. The brush has a first end, a second end, and a metal core, the metal core defining a longitudinal axis extending throughout the brush. The flexible metal leader has a first end and a second end, the second end of the flexible metal leader being welded to the first end of the metal core of the brush. The flexible metal leader is adapted to be fed through the lumen of the surgical instruments and pulled by the first end thereof through the lumen, with the brush also being adapted to be pulled through the lumen due to its being welded to the second end of the flexible metal leader.

21 Claims, 12 Drawing Sheets

SCRUBBING ELEMENT WITH WELDED WIRE LEADER

RELATED APPLICATIONS

This application is a continuation-in-part of U.S. patent application Ser. No. 10/403,133, filed Mar. 31, 2003 now abandoned, and which application is hereby incorporated by reference herein in its entirety.

FIELD OF THE INVENTION

The present invention relates generally to cleaning elements and methods for using the elements for cleaning surgical devices, and more specifically, to flexible cleaning elements for use in connection with cleaning surgical instruments having lumens or other similar configurations, and to methods for using such cleaning elements for cleaning such surgical instruments.

BACKGROUND OF THE INVENTION

The present invention is in the field of cleaning surgical instruments, such as flexible and nonflexible endoscopes, surgical lumens, and other medical paraphernalia used in healthcare facilities. This cleaning typically takes place as a preliminary step subsequent to use and soiling of the surgical instruments, and prior to their sterilization.

The physical designs of most models of endoscopes do not make possible the cleaning of every internal surface. It has been a common practice to merely soak used surgical instruments such as biopsy channels or lumens in a detergent bath and scrubbing with a small scrub brush prior to their being sterilized. Since delicate material is often used to make flexible endoscopes, scrub brushes longer than about 2.0 cm have a tendency to damage the lumen. Moreover, small scrub brushes cannot thoroughly scrub the internal surfaces of surgical lumens resulting in contaminants remaining throughout surgical lumens. Pushing a scrub brush through a lumen is also problematic because it may damage the lumen wall.

There is concern about the transmission of diseases that commonly arise in healthcare facilities, and by viruses carried in tissues and blood, such as hepatitis C and HIV, which may be transmitted to other patients or personnel dealing with soiled surgical instruments such as most models of flexible endoscopes. This concern stems from the difficulty in cleaning surgical lumens by a method meticulous enough to scrub a soiled lumen, while at the same time being simple and straightforward enough to be utilized by personnel requiring a minimum amount of training, and using an apparatus which is both inexpensive and reliable. Moreover, it is problematic that surgical lumens and other paraphernalia may be grossly soiled, and therefore require vigorous cleaning throughout the entire length of the surgical lumen, both inside and out. Unfortunately, cleaning agents and brushes are not available which easily accomplish the vigorous cleaning of soiled surgical lumens prior to their microbiological decontamination. This problem is compounded by the fact that cleaning brushes are usually incompatible with flexible surgical lumens. Thus, heretofore, it has not been easy to clean the inside of deep surgical lumens using an elongated brush as described herein.

A number of different methods are known in the art for cleaning surgical instruments and other medical paraphernalia. For example, U.S. Pat. No. 4,867,797 herein incorporated by reference discloses a method for cleaning instruments used for analyzing protein-containing biological liquids which utilizes an enzyme rinse solution, but uses germicides therewith only in low concentrations and only to increase the stability of the enzyme composition by protecting it against microbial deterioration.

U.S. Pat. No. 6,224,544 relates to an endoscope, being insertable in the colon of a patient, in a self-propelled manner, by driving a plurality of endless belts mounted along the outside surface of a flexible section of an insertion tube thereof, and having a cleaning mechanism therein to be easily cleaned after use. The insertion tube, operation unit, and a lower portion of the driving unit casing are cleaned by immersion in a washing vessel filled with a cleaning solution.

U.S. Pat. No. 5,489,531 herein incorporated by reference relates to a two-stage method using the same container for both cleaning and microbiologically decontaminating grossly soiled surgical instruments. A presoak in an enzyme solution is followed by direct addition of a compatible disinfectant and a continued soak to decontaminate surgical instruments and other paraphernalia used in healthcare facilities.

Longitudinal brushes having a twisted wire core are known, such as, for example, mascara brushes used to apply mascara to a user's eyelashes. A typical mascara brush is made of a core formed from a single metallic wire folded in a generally u-shaped configuration to provide a pair of parallel wire segments. Bristles, usually made of strands of nylon, are disposed between a portion of a length of the wire segments. The wire segments are then twisted, or rotated, about each other to form a helical core (also known as a twisted wire core) that holds the filaments substantially at their midpoints so as to clamp them. In this way, a bristle portion or bristle head is formed with radially extending bristles secured in the twisted wire core in a helical or spiral manner. See, for example, U.S. Pat. No. 4,887,622, U.S. Pat. No. 4,733,425, and U.S. Pat. No. 6,481,445 all of which are herein incorporated by reference.

It is problematic that unclean instruments cannot be properly disinfected or sterilized. Moreover, the physical properties of endoscope tubing and the designs of some complex surgical instruments contribute to limiting the effectiveness and reliability of brush devices, detergent systems, and increases the probability that a lumen's internal surfaces may remain contaminated following state-of-the-art cleaning. Accordingly, what is needed is a cleaning brush that provides a simple, cost efficient mechanism for cleaning surgical instruments by providing direct access to the internal surface, as well as cleaning brush kits and systems, which deliver cleaning solution directly to the deep channels of the lumens.

It is also problematic that a brush portion of a cleaning element may not be adequately attached to a handle portion of the cleaning element. This may be particularly problematic in situations, such as those disclosed in U.S. Pat. No. 5,615,439, where the core of the brush portion of the cleaning element may be made from one material (e.g., metal), while the handle portion of the cleaning element is made from some other material (e.g., plastic). In such situations, it is often difficult to achieve an adequate bonding between the brush portion and the handle portion so as to ensure that the parts do not come detached from one another. Such is particularly undesirable when instruments having long, thin lumens are being cleaned, since, if the brush comes detached from the handle while the brush portion is located completely within the lumen, it may be extremely difficult, if not impossible, to remove the brush portion from the lumen without damaging the lumen, thereby causing a waste of time and effort, and possibly rendering the instrument unusable.

SUMMARY OF THE INVENTION

Accordingly, it is an object of the present invention to provide a cleaning element, which is durable and flexible.

Accordingly, it is an object of the present invention to provide a cleaning element that provides a simple, cost efficient mechanism for cleaning surgical instruments by providing direct access to the internal surfaces of a lumen.

Accordingly, it is an object of the present invention to provide a cleaning element that increases the effectiveness and reliability of brush devices, and detergent systems.

Accordingly, it is an object of the present invention to provide a cleaning element that decreases the probability that a lumen's internal surface may remain contaminated following cleaning.

Accordingly, it is an object of the present invention to provide a cleaning element and methods of use thereof that promote sterilization through thorough cleaning.

Accordingly, it is an object of the present invention to provide a cleaning element and methods of use thereof that remove and dissolve, blood, fat, proteins, mucous and other organic contaminates from soiled surgical instruments and lumens.

Accordingly, it is an object of the present invention to provide a cleaning element and methods of use thereof that maintain contact and positive pressure between enzyme and lumen during soaking cycle.

Accordingly, it is an object of the present invention to provide a cleaning element and methods of use thereof comprising a full-length cylindrical bristle portion of brush, which effectively removes residual debris from interior of soiled lumens or surgical instruments.

Accordingly, it is an object of the present invention to provide a cleaning element and methods of use thereof that do not damage instrument seals or rings.

Accordingly, it is an object of the present invention to provide a cleaning element and methods of use thereof that prevent corrosion of stainless steel and carbon steel surgical instruments.

Accordingly, it is an object of the present invention to provide a cleaning element and methods of use thereof that increase the effectiveness of the enzyme/surfactant cleaning properties.

Accordingly, it is an object of the present invention to provide a cleaning element and methods of use thereof that increases effectiveness of decontamination and sterilization of precleaned surgical instruments.

Accordingly, it is an object of the present invention to provide a cleaning element that decreases the probability that a brush portion thereof will unintentionally become detached from a handle portion thereof.

These and other objects of the present invention are achieved, in accordance with one embodiment of the present invention, by provision of a cleaning element for lumen of surgical instruments, which cleaning element includes a brush and a flexible metal leader. The brush has a first end, a second end, and a metal core, the metal core defining a longitudinal axis extending throughout the brush. The flexible metal leader has a first end and a second end, the second end of the flexible metal leader being welded to the first end of the metal core of the brush. The flexible metal leader is adapted to be fed through the lumen of the surgical instruments and pulled by the first end thereof through the lumen, with the brush also being adapted to be pulled through the lumen due to its being welded to the second end of the flexible metal leader.

In some embodiments, the flexible metal leader comprises metal wire or twisted metal wire segments. In certain of these embodiments, the flexible metal leader is formed from soft steel or iron. In certain of these embodiments, the flexible metal leader comprises stainless steel braided wire. In some embodiments, the metal core of the brush comprises a pair of twisted metal wire segments. In certain of these embodiments, the brush further comprises a plurality of bristles secured between the pair of twisted wire segments. In some embodiments, the second end of the flexible metal leader is welded to the first end of the metal core of the brush by at least one of the following welding techniques: spot welding, arc welding, oxy-acetylene welding, electron beam welding, plasma beam welding, cold-press welding, friction welding, and ultrasonic metal welding.

In some embodiments, the flexible metal leader and the weld between the flexible metal leader and the metal core of the brush have smooth outer surfaces, thereby reducing the likelihood of damage to the lumen of the surgical instruments during cleaning thereof. In some embodiments, the cleaning element further includes a jacket or coating covering the flexible metal leader and the weld between the flexible metal leader and the metal core of the brush. In certain of these embodiments, the brush further comprises a plurality of bristles, and the jacket or coating covers a portion of the bristles of the brush and has an end terminating in an area adjacent to the bristles of the brush. In certain embodiments, the brush further comprises a plurality of bristles, and the jacket or coating has an end terminating in an area adjacent to the metal core of the brush such that the jacket or coating does not cover a portion of the bristles of the brush. In certain embodiments, the jacket or coating is formed from a polymer material. In certain of these embodiments, the jacket or coating is formed from nylon.

In accordance with another embodiment of the present invention, a cleaning element for lumen of surgical instruments includes a brush and a flexible metal leader. The brush has a first end, a second end, and a metal core, the metal core defining a longitudinal axis extending throughout the brush. The flexible metal leader has a first end and a second end, the second end of the flexible metal leader being welded to the first end of the metal core of the brush. The cleaning element also includes a jacket or coating covering the flexible metal leader and the weld between the flexible metal leader and the metal core of the brush.

In some embodiments, the brush further comprises a plurality of bristles, and the jacket or coating covers a portion of the bristles of the brush and has an end terminating in an area adjacent to the bristles of the brush. In some embodiments, the brush further comprises a plurality of bristles, and the jacket or coating has an end terminating in an area adjacent to the metal core of the brush such that the jacket or coating does not cover a portion of the bristles of the brush. In some embodiments, the jacket or coating is formed from a polymer material. In certain of these embodiments, the jacket or coating is formed from nylon.

In some embodiments, the flexible metal leader is adapted to be fed through the lumen of the surgical instruments and pulled by the first end thereof through the lumen, with the brush also being adapted to be pulled through the lumen due to its being welded to the second end of the flexible leader In some embodiments, the flexible metal leader comprises metal wire or twisted metal wire segments. In certain of these embodiments, the flexible metal leader is formed from soft steel or iron. In certain of these embodiments, the flexible metal leader comprises stainless steel braided wire. In some embodiments, the metal core of the brush comprises a pair of twisted metal wire segments. In certain of these embodiments, the brush further comprises a plurality of bristles secured between the pair of twisted wire segments. In some embodiments, the second end of the flexible metal leader is welded to the first end of the metal core of the brush by at least one of the following welding techniques: spot welding, arc welding, oxy-acetylene welding, electron beam welding, plasma beam welding, cold-press welding, friction welding, and ultrasonic metal welding.

In accordance with another aspect of the present invention, a method of forming a cleaning element for lumen of surgical instruments comprises the steps of: (i) providing a brush having a first end, a second end, and a metal core, the metal core defining a longitudinal axis extending throughout the brush; (ii) providing a flexible metal leader having a first end and a second end; (iii) welding the second end of the flexible metal leader to the first end of the metal core of the brush; and (iv) providing a jacket or coating covering the flexible metal leader and the weld between the flexible metal leader and the metal core of the brush.

In some embodiments, the method further comprises the steps of: (v) feeding the flexible metal leader through the lumen of a surgical instrument; and (vi) pulling the flexible metal leader by the first end thereof through the lumen, with the brush also being pulled through the lumen due to its being welded to the second end of the flexible leader. In some embodiments, the welding step employs at least one of the following welding techniques: spot welding, arc welding, oxy-acetylene welding, electron beam welding, plasma beam welding, cold-press welding, friction welding, and ultrasonic metal welding.

In accordance with another aspect of the present invention, a kit for cleaning a soiled lumen having a first end and a second end comprises a cleaning element according to one of the embodiments described above, a pouch having an inner space for holding liquid solution, and a liquid cleaning solution.

The term "surgical instruments" as used herein means any of those instruments commonly used in a wide variety of surgical procedures, whether in a hospital operating room environment or in a doctor's office on an outpatient basis. Such instruments are, for the most part, made of surgical quality stainless steel, but they may be composed of other materials as well, e.g., aluminum and polypropylene and other polymer materials. In addition, the term "surgical instruments" includes other medical and surgical paraphernalia which might not typically be considered a surgical instrument, but which comes into contact with human tissue, especially blood, during a surgical or some other medical procedure, during the course of which that item of medical or surgical paraphernalia becomes grossly soiled and microbiologically contaminated. Examples of such medical and surgical paraphernalia are cardiovascular instruments, eye instruments, micro-surgical instruments, neurologic and orthopedic instruments, laparoscopes, flexible fiberoptic scopes, endoscopes, bronchoscopes, cystoscopes, colonoscopes, and respiratory therapy equipment.

The terms "grossly soiled" and "substantially soiled" as used herein mean the condition of being contaminated to a substantial extent by contact with human tissue, fluids, excretia, and so forth, as the result of contact therewith during some surgical or other medical procedure. Contamination by contact with human blood in substantial amounts is particularly referred to, and this includes microbiological contamination by viruses and bacteria contained in that blood. A surgical instrument that is "grossly soiled" is one that requires a step of cleaning prior to reuse. The step of cleaning removes or lifts the human tissue, fluids, excretia, etc. which have adhered to the surgical instrument, but provides little or no microbiological decontamination of the viruses, bacteria or other microorganisms present in that human tissue, fluids, excretia, etc., which have also adhered to the surgical instrument to be cleaned. For these, the further step of microbiological decontamination is needed.

The term "lumen" means the bore of a tube. The term also means tubing of or from a surgical instrument as defined above. In addition, the term includes 'biopsy channel' and other medical and surgical tubing which might not typically be considered a lumen, but which comes into contact with human tissue, especially blood, during a surgical or some other medical procedure, during the course of which that item of medical or surgical tubing becomes grossly soiled and/or microbiologically contaminated.

As used herein, the term "hydrophilic", when used in connection with a solid, means capable of being readily wet by water. When used in connection with a liquid, the term "hydrophilic" means the liquid is miscible in water or aqueous solutions.

As used herein "enzyme-based cleaning compositions" refers to cleaning compositions designed to remove substantially all human tissue, fluids, excretia, etc. from grossly soiled metal and other surfaces, especially surgical instruments and other medical paraphernalia, in which the enzyme is selected from protease, lipase, amylase, carbohydrase or other enzymes or combinations of enzymes and surfactants known to break down blood, body tissue and excretia.

The term "germicidal detergent microbiological decontamination composition" refers to germicidal detergents especially designed to provide microbiological decontamination of all grossly soiled metal and other surfaces, especially surgical instruments and other medical paraphernalia, selected from phenolic compounds, quaternary amines, glutaraldehyde and other known disinfectants or combinations thereof.

As used herein the "urethane" is an ester of carbamic acid; also a monoester, monoamide of carbonic acid.

The invention and its particular features and advantages will become more apparent from the following detailed description considered with reference to the accompanying drawings.

DETAILED DESCRIPTION OF AN EMBODIMENT OF THE INVENTION

Figure 1:
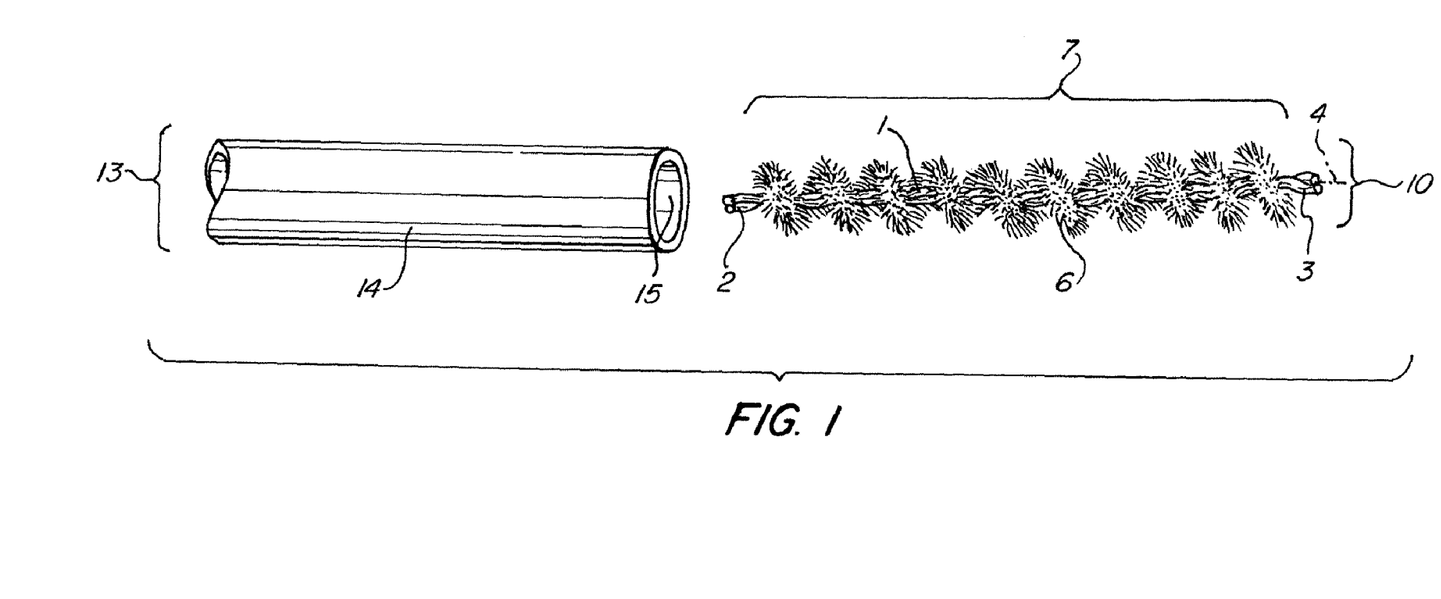
FIG. 1 is a side view of a brush in accordance with the present invention showing the bristle portion in representative form and further provides a side view of a lumen.

Referring now to FIG. 1, brush 10 is an elongated brushlike structure having a deformable core 1 of wire or other material. The brush 10 is intended for use in an instrument of the type having a tube 14 defining a lumen 13 with a first opening 15 to tube 14 dimensioned to receive brush 10. Brush 10 is comprised of a central core 1 or flexible wire having a first or proximal end 2, and a second or distal end 3 opposite the first end 2 in which bristle 6 of tufted fabric is twisted to form a bristle portion 7. A longitudinal axis 4 is defined along core 1 through first and second ends, 2 and 3, respectively. Bristle portion 7 extends along at least part of the length of the core 1 from first end 2 toward second end 3. Brush 10 is comprised of radially extending bristles 6 attached to core 1. Core 1 may be a twisted wire core made by first forming a pair of parallel wire segments 21 (FIG. 5) connected at one end 22 to form a "U". Preferably, core 1 is interwoven with bristle 6 material to form a pipe cleaner type cleaning element.

Bristle 6 may be made by any known technique and from a variety of materials. For example, bristle 6 may be made from polyester, polypropylene, cotton, woven fabrics, non-woven fabrics, nylon or polyamide derivatives, thermoplastic elastomers, and combinations of these. Bristle 6 may be manufactured to a desired length, or may be cut to a desired length from a continuous filament. Bristle 6 or continuous filament may be selected from any one of a number of commercially available products that are made from a relatively soft thermoplastic elastomer material having various tear strengths, densities, and hardness. It is important that bristle 6 be flexible enough to be compressed when bristle portion 7 is squeezed between fingers of the user of any embodiment.

One preferred embodiment utilizes a less flexible core 1 by making brush 10 with a stiffer wire e.g. 0.02 inch diameter. Such an embodiment is desirable for cleaning stainless steel surgical instruments. It has been found that using a polyester yarn to form bristle 6 makes brush 10 more durable for this embodiment. Moreover, it has been found that a polyester yarn is a preferred substrate for applying a hydrophilic polymer such as hydrophilic urethane for this embodiment.

Figure 2A:
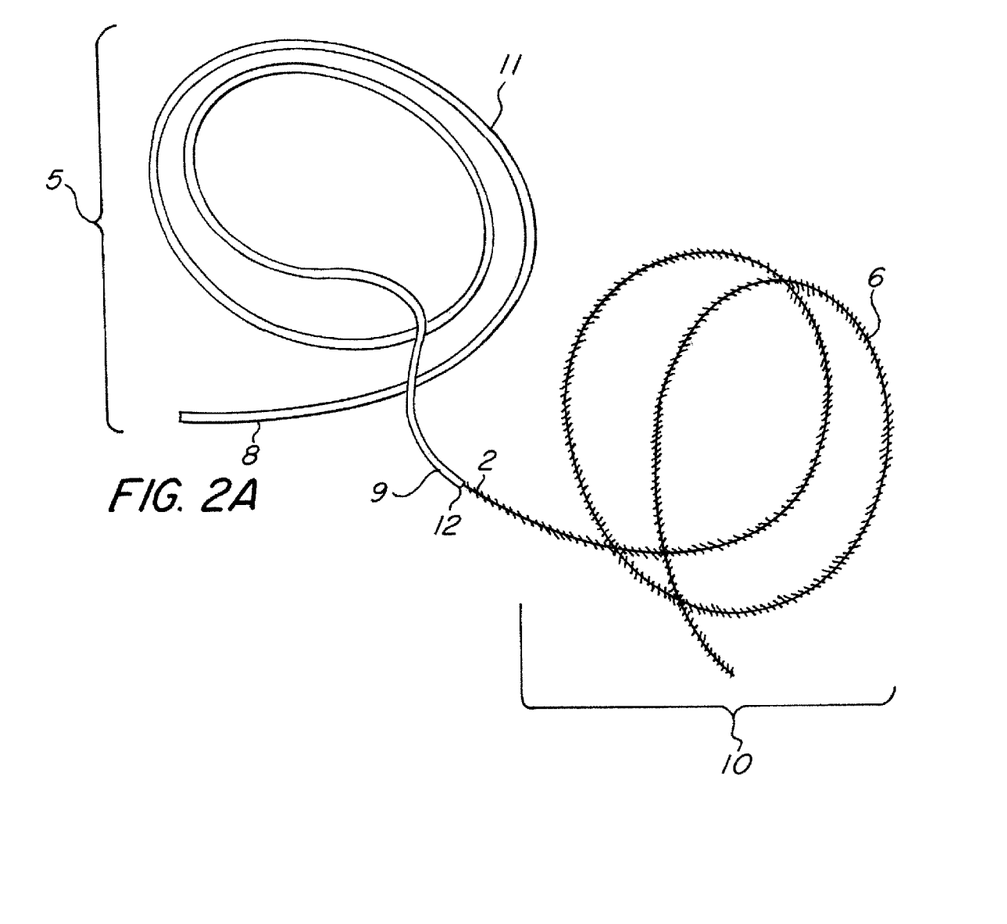
FIG. 2A is a side view of a brush with leader in accordance with one embodiment of the present invention showing the bristle portion in representative form.
Figure 2B:
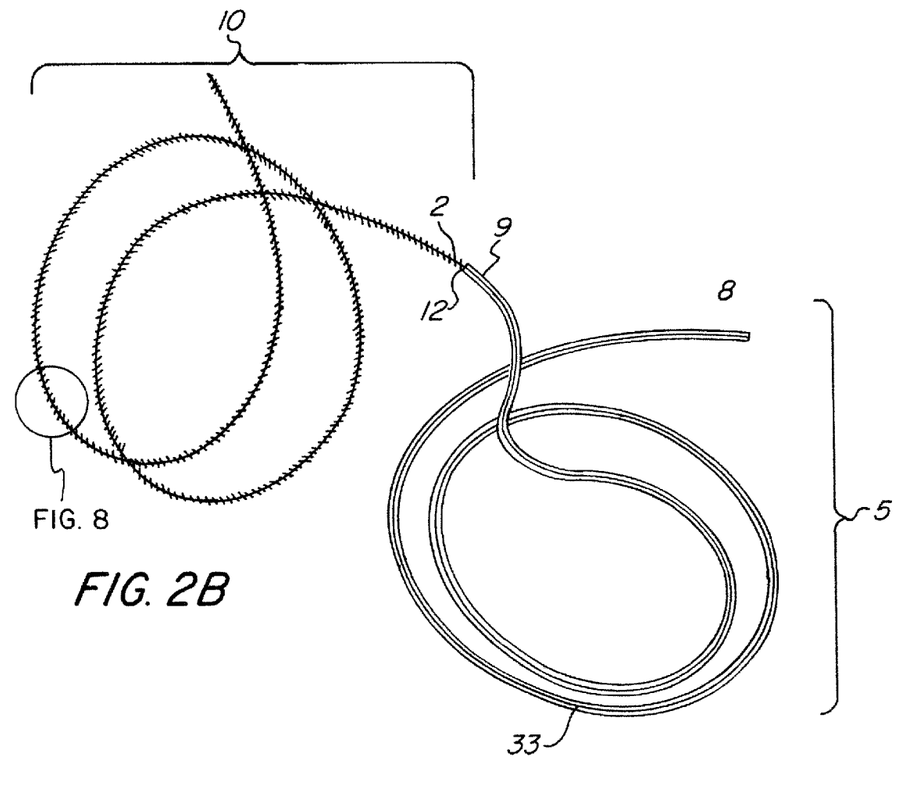
FIG. 2B is a side view of a brush with a leader in accordance with one embodiment of the present invention showing the leader portion in a form different than FIG. 2A.
Figure 3:
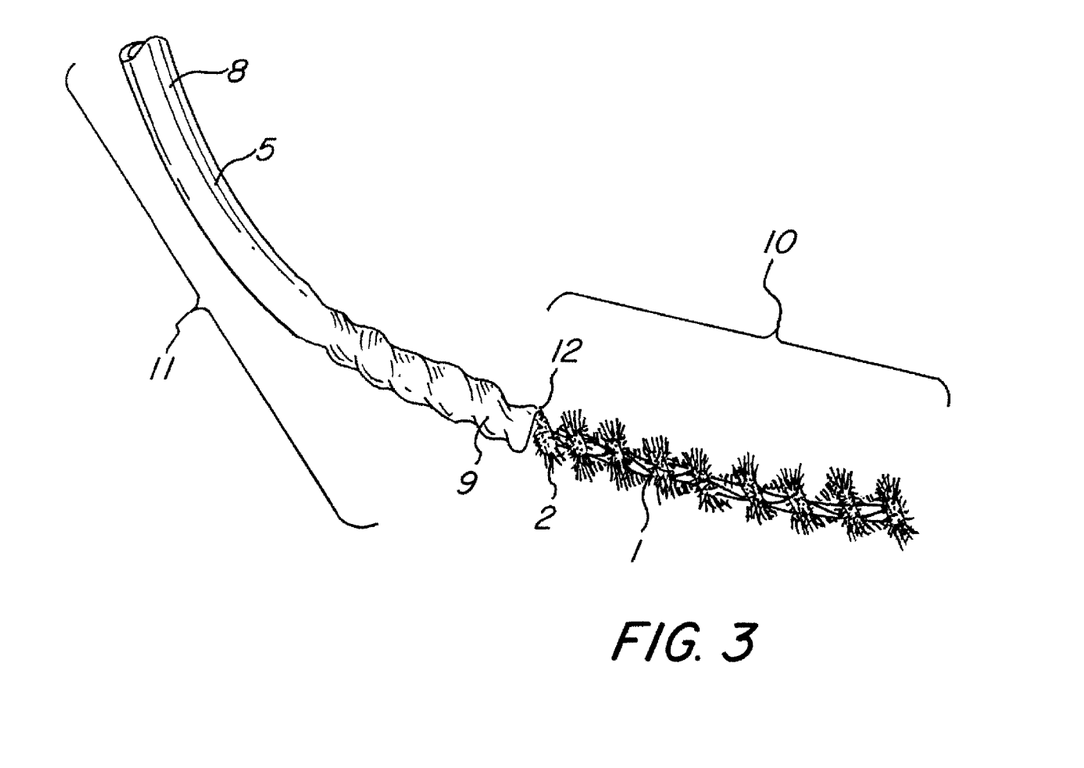
FIG. 3 is a more detailed side view of a brush with leader as shown in FIG. 2A.

Referring to FIGS. 2A, 2B and 3, another preferred embodiment utilizes a more flexible core 1 by assembling brush 10 with a flexible wire e.g. 0.014 inch diameter and/or 0.016 inch diameter. Such embodiments are desirable for cleaning flexible surgical instruments or lumens, and preferably utilize a polyester and/or polypropylene yarn to form bristle 6 on brush 10.

Figure 8:
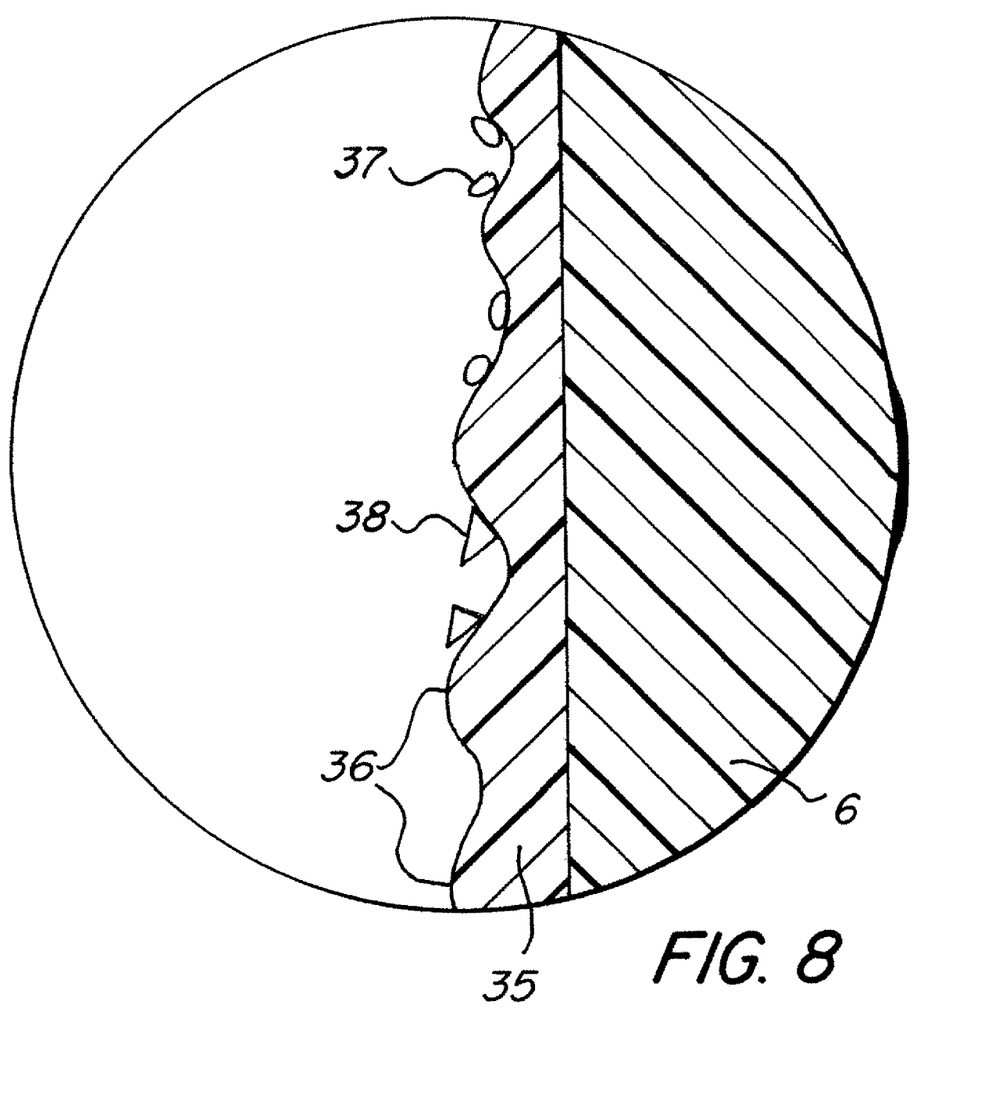
FIG. 8 is an enlarged view of a bristle portion of the brush with leader of FIG. 2B.
Figure 9:
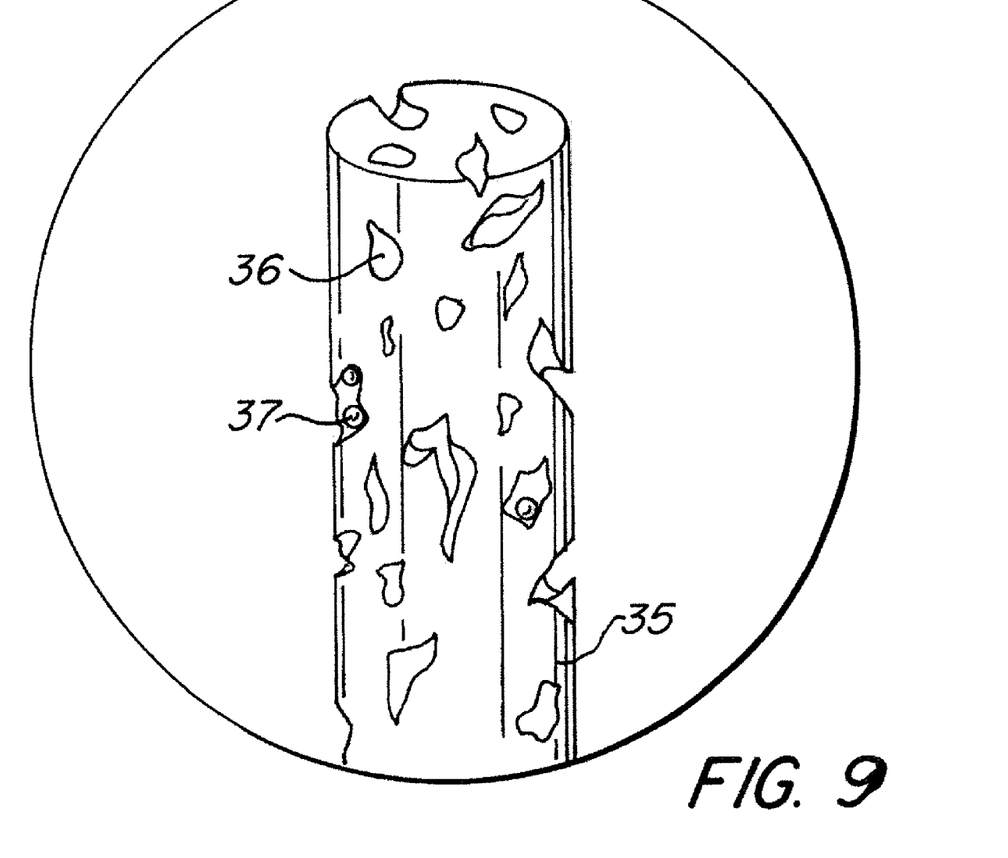
FIG. 9 is an enlarged view of a single bristle covered by a coating layer of the brush of FIG. 1.

Referring now to FIGS. 8 and 9, one embodiment of the present invention provides a coating layer 35 on bristle 6 preferably comprising a hydrophilic polymer. In one embodiment, coating layer 35 preferably comprises a hydrophilic polymer such as hydrophilic urethane. Although not wishing to be bound by this disclosure, it is believed that providing a coating layer 35 on bristle 6 increases the surface area of bristle 6 and improves water absorption properties. Furthermore, coating layer 35 provides one or more pores or reservoirs 36. These pores 36 or reservoirs may hold cleaning solution 37, agents and mixtures thereof. Cleaning solution 37 does not wash out easily from the bristle 6 or bristle portion 7 because it is entrained throughout all the interstitial small pore spaces 36 of bristle 6. Such a design makes available the premanufacturing of cleaning elements of the present invention loaded with non-ionic detergents and a variety of multitier enzymes designed to target the most common bio-burden of flexible endoscopes, or lumens. Pore 36 may also hold disinfectant 38.

Materials suitable as cleaning agent 37 for the cleaning element of the present invention are manifold, provided that the materials are capable of promoting debris removal from grossly soiled and/or substantially soiled surgical instruments. Examples of such materials include detergents e.g. nonionic detergent. Suitable nonionic detergent active compounds can be broadly described as compounds produced by the condensation of alkylene oxide groups, which are hydrophilic in nature, with an organic hydrophobic compound which may be aliphatic or alkyl aromatic in nature. Such non-ionic detergents are readily known in the art and partially described in U.S. Pat. No. 6,492,321 herein incorporated by reference. It is also possible to include cationic, anionic, amphoteric, or zwitterionic detergent actives, or combinations of these, in the cleaning element according to the invention, however these are less preferable since they may break down the enzymes that may be present in the cleaning solution. Many suitable detergents are commercially available. It is believed that non-ionic detergents have a lower surface tension than water which helps to lift debris from surface of grossly or substantially soiled medical instruments. For example, nonionic detergent, and a wetting agent, will lift blood from the surface of a medical instrument, and break the blood apart in solution.

Additional materials suitable as cleaning agent 37 include enzyme-based cleaning compositions. These enzyme-based cleaning compositions are well known in the art and are commercially available. The enzyme-based cleaning composition may have a number of additional ingredients which help promote its effectiveness and use, e.g., other cleaning agents such as sodium tetraborate, emulsifiers such as triethanolamine, solvent thickeners such as propylene glycol, acidifiers such as citric acid, buffering agents, preservatives, and so forth. Such excipients would be well known to one of ordinary skill in this art. However any enzymatic cleaner, which promotes the removal of protein, blood, mucus, feces, urine, albumin, etc., from medical apparatus and instruments would be suitable.

Another embodiment of the present invention may further provide a disinfectant 38 or germicidal detergent microbiological decontamination composition applied to coating layer 35, or polymer layer. As shown in FIG. 8 disinfectant is preferably entrained throughout interstitial small pores 36 or reservoir spaces on coating layer of bristle 6. The disinfectant, i.e., the germicidal detergent decontaminating composition may have a number of additional ingredients which help promote its effectiveness and use, e.g., strong acids and bases such as phosphoric acid and caustic soda, emulsifiers and surfactants such as □-olefin sulfonate, and various fragrances which help to mask the odor of the phenolic compounds.

Referring now FIGS. 2A, 2B and 3, brush 10 is shown attached to lead or leader 5. Leader 5 may be made by any known techniques and from a variety of materials. For example, leader 5 may be made from polyvinyl chloride, polystyrene, polyethylene, polyethylene terephthalate, rubber, natural rubber latex, acetal, butyrate, cast acrylic, ECTFE, extruded acrylic, polycarbonate, polyethylene, polypropylene, polysulfone, PVDF, nylon, polyurethane, thermoplastic (styrene-, propylene- and urethane-based) elastomers, and even the high-performance specialty resins such as silicone and fluoropolymers, as well as combinations of these materials. Leader 5 may be made from any suitable resin, plastic, or thermoplastic elastomer, and combinations thereof. Preferably, leader 5 is made out of flexible polyvinyl chloride (PVC). Leader 5 may be made out of wire, or twisted wire segments. Leader 5 may be made out of a polymer thread similar to fishing wire. Leader 5 is typically flexible tubing precut to a desired length. Leader 5 has a proximal end 8 or first end, and distal end 9 or second end. The body portion 11 extends from first end 8 toward second end 9. Body portion 11 may be hollow. Leader 5 is typically between 0.2 m to 4 m in length from first end 8 to second end 9. Preferably leader 5 is long enough to be passed all the way through a lumen of known length. For example, if a lumen (not shown) for a colonoscope is 2 m in length, leader 5 would preferably be longer than 2 m in length, so that a user can pass first end 8 all of the way through the inside of the lumen so that the first end 8 extends out of the lumen opposite the receiving end of the lumen, while second end 9 remains below the receiving end of the lumen. Leader 5 may be substantially equal in length to brush 10 and brush portion 7. For example, if brush 10 is 2.0 m in length, leader 5 may be about 2.3 m in length. Leader 5 is of a predetermined diameter. The diameter of leader 5 is smaller than the diameter of the lumen so that leader 5 can pass through the inside of the lumen in which it has been inserted. Leader 5 has a diameter of from about 1.5 mm to about 6.0 mm, preferably about 1.5 mm to about 2.7 mm. Preferably leader 5 is about equal in length to brush 10 and brush portion 7. Leader 5 may be a hollow tube. Leader 5 is preferably cylindrical in shape.

Figure 10:
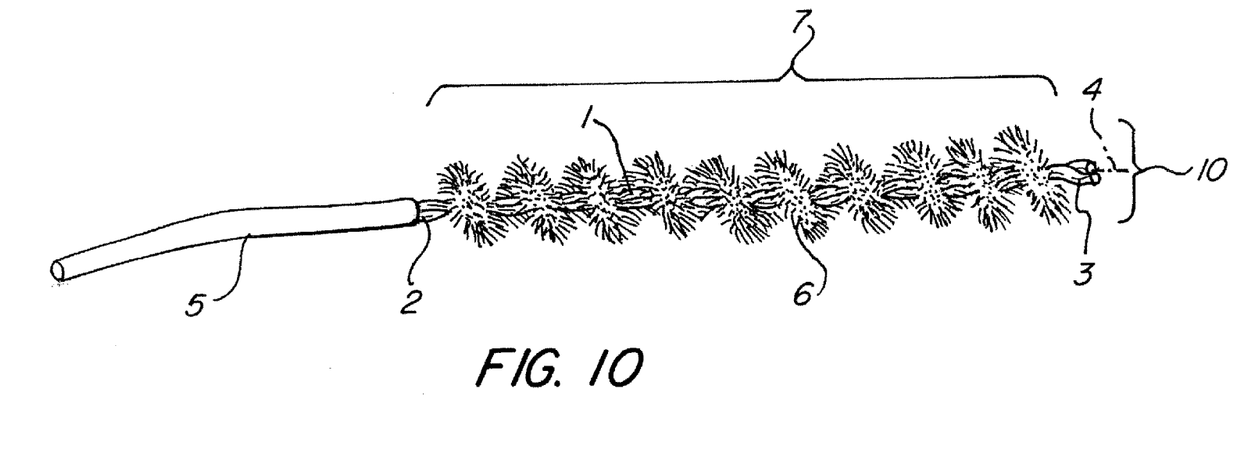
FIG. 10 is a side view of a brush with leader different than the embodiment shown in FIG. 2A.

It is important that leader 5 be made of material stiff enough to pass it through a soiled lumen. The desired stiffness may be achieved by utilizing a stiff polymer to form body portion 11, e.g. PVC, or nylon. Support wire 33 may also be inserted within body portion 11 to increase rigidity of leader 5. Referring to FIG. 2(B), wire 33 is shown within leader 5. Wire 33 is of a type that is well known in the art, e.g., a conventional soft steel or iron wire, the dimensions and specifications of which are also well known. Wire 33 may be a 0.014 to 0.016 inch diameter wire, within the hollow body portion 11, however, any diameter wire may be utilized so long as it is able to flexibly pass through soft lumen tubing without damaging the lumen walls. Wire 33 preferably is of preselected length, however, preferably about equal in length to leader 5. Most preferably it is slightly shorter than leader 5 (within about 1 cm) so that it can lie within body portion 11, and proffer increased rigidity throughout the length of leader 5. Wire 33 is preferably a stainless steel braided wire with a nylon jacket or coating. Leader 5 may be entirely made up of wire 33 and attached directly to the core of brush portion as shown in FIG. 10. In such cases, leader 5 is preferably coated with a polymer layer or jacket preferably made of nylon.

FIGS. 2A, 2B and 3 show brush 10 attached to leader 5. Typically second end 9 of leader 5 is attached to first end 2 of core 1 to form joint 12. Joint 12 may be made by any known techniques using a variety of materials. For example, second end 9 may be tied onto the first end 2 of core 1 using a tie, string, or wrap (not shown). Alternatively, first end 2 of core 1 may be wrapped around second end 9 so that the two pieces are tied together. Moreover, first end 2 of core 1 and second end 9 may be bonded by utilizing a heat shrink wrap (not shown). Preferably the two ends are jointed using a bonding resin or adhesive cement. For example, Super Glue® or Krazy Glue® brand adhesives may be utilized to form a bond. This type of bond is preferable since it allows the tips of both first end 2 and second end 9 to be bond directly together, avoiding a bulge that may form when other bonding methods are employed.

Figures 4A, 4B:
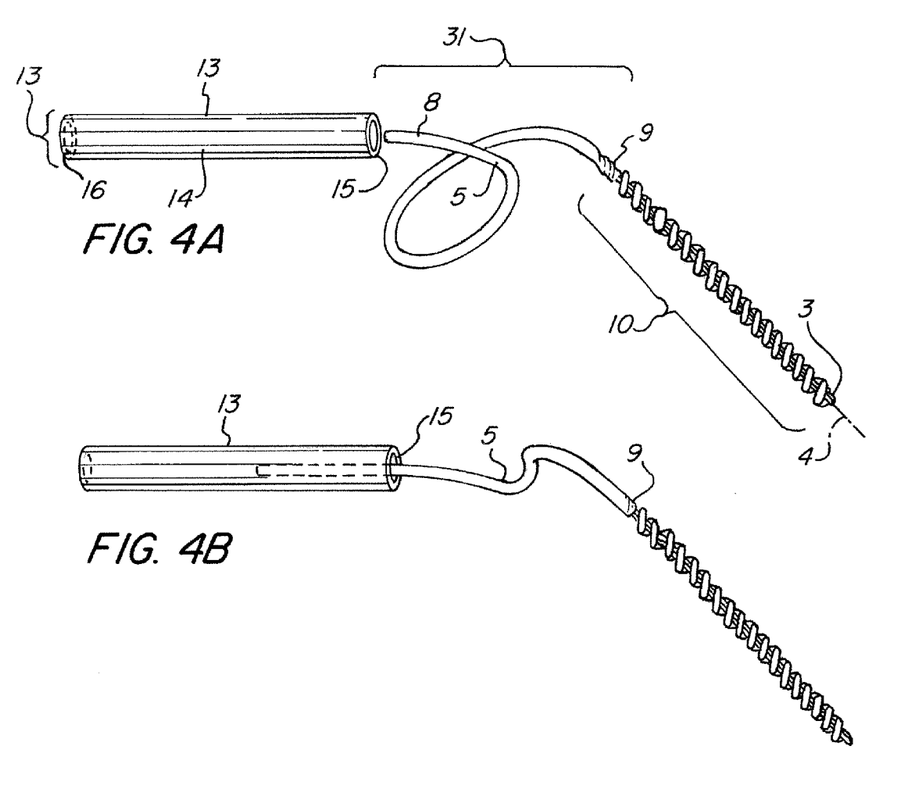
FIGS. 4A-4D are perspective side views illustrating steps in the process of cleaning a surgical instrument of one embodiment of the present invention.
Figure 4C:
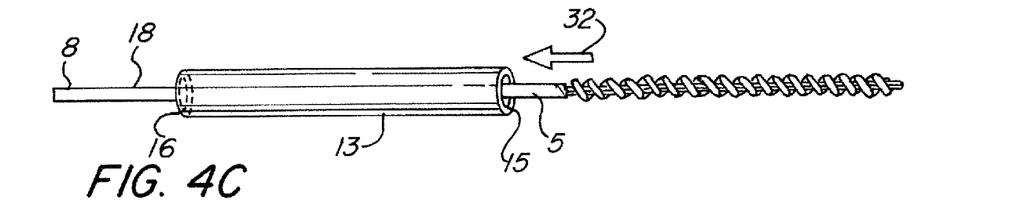
Figure 4D:
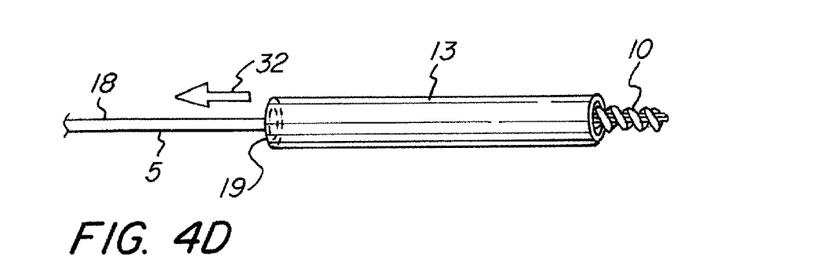

FIGS. 4A-4D show a method of using cleaning elements of the present invention. FIG. 4A shows cleaning element 31 with leader 5 next to a substantially soiled or grossly soiled lumen 13. Although not shown in the present drawings, lumen 13 is soiled and debris may randomly coat the inner walls of tube 14. In order to clean lumen 13 one must provide a cleaning element 31 of the present invention having brush 10, first end 2, second end 3, and a core 1, core 1 defining a longitudinal axis 4 extending throughout the length of brush 10; and leader 5 having first end 8, and second end 9. Second end 9 of leader 5 is connected to first end 2 of brush 10. FIG. 4B shows the step of inserting leader 5 into first end 15 of lumen 13. FIG. 4C shows the step of passing first end 8 of leader 5 through lumen 13 to create exposed leader portion 18, after distal lumen opening 16. Arrow 32 shows the direction of the movement of leader 5 through lumen 13. Even after leader 5 is passed through lumen 13, leader 5 is still visible below first end 15 of lumen 13. FIG. 4D shows the step of pulling exposed leader portion 18 away from second end 19 so brush 10 passes through lumen 13. Arrow 32 shows the direction of the movement of brush 10 through lumen 13, and confirms that the brush is being pulled through lumen 13. It has been surprisingly found that pulling the cleaning element of the present invention increases debris removal from soiled surgical instruments and lumen.

Other embodiments include the step of adding cleaning solution described above into lumen, as well as soaking the inserted cleaning element and lumen for two to five minutes in a bath to ensure that the brush 10 maintains positive contact with the interior walls of lumen 20 throughout the length of the channel. The soaking step further includes providing nonionic detergents and a variety of enzymes designed to target the most common bio-burden of endoscopes and surgical lumens. As a dry, pre-dosed product, other embodiments of the claimed invention include storing the cleaning elements near the point of use and utilizing the cleaning element immediately after a procedure is performed with a surgical instrument. Other methods of use embodiments include the steps of wetting a soiled surgical instrument with tap water and inserting cleaning element into lumen. After soaking, the cleaning element is used to thoroughly brush the channel and remove debris such as protein, blood, mucus, feces, urine, albumin, etc., from all medical apparatus and surgical instruments.

Figure 5:
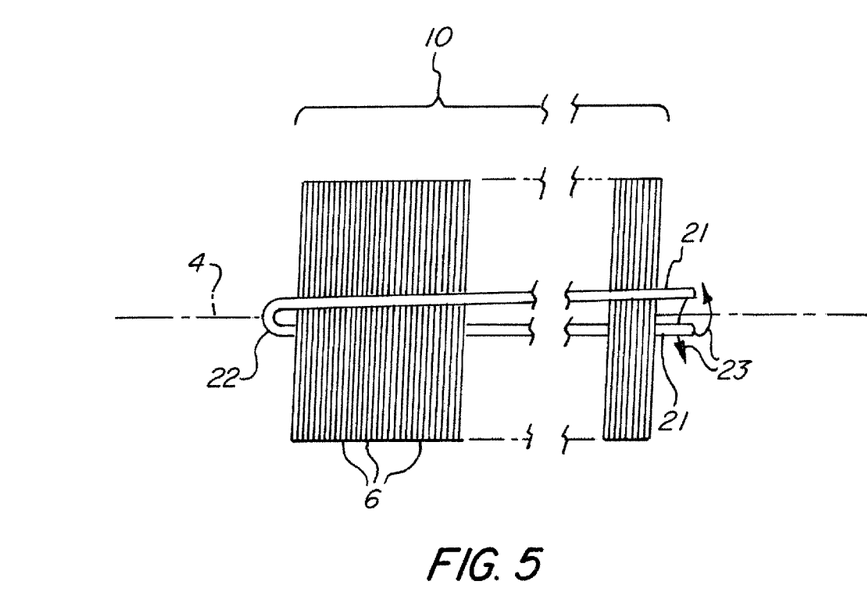
FIG. 5 is a perspective side view of a step in the process of making a brush of the type embodying the invention.

Referring back to the drawings, FIG. 5 shows a method for making brush 10 in accordance with the present invention. Core 1 (not shown) is a twisted wire core typically made by first forming a pair of parallel wire segments 21 connected at one end 22 to form a "U". The wire is of a type that is well known in the art, e.g., a conventional soft steel or iron wire, the dimensions and specifications of which are also well known. A plurality of bristles 6 of a selected length and material (such as polyester or polypropylene) are placed between the pair of wire segments 21. The wire segments 21 are then twisted about the longitudinal axis 4 (see arrows 23 in FIG. 6) to secure in clamping engagement each of the bristles 6 at approximately a midpoint of bristle 6. In this way, opposite ends of each bristle 6 extend radially from the twisted wire core. After the bristles 6 are secured, the brush head may be trimmed by any suitable means, e.g., grinding, laser cutting, etc., to have any desired shape, e.g., cylindrical, tapered, conic, bi-conic, etc. Preferably the shape is cylindrical to ensure that greatest area of contact between brush 10, and the lumen 13 (of FIG. 1.). Most preferably, the brush portion may be made similar to how a pipe cleaner (e.g. for cleaning tobacco pipe) is made. Here the cleaning element is made in a continuous process using yarn instead of cut bristles, and the wire is not turned back on itself. Rather wire is interwoven with the yarn. This may be done using 50 to 2000 linear feet of yarn at one time.

Referring again to FIGS. 8 and 9, brush 10 of the present invention may be further modified by coating bristle 6 with a coating layer 35, such as a hyprophillic polymer, e.g. hydrophillic urethane. Such embodiments may be formed by providing liquid coating solution such as hydrohillic polymer, prepared by any conventional technique. Moreover, a tub is provided long enough to hold a substantially straight brush. Tub may be between 0.1 m to 6 m in length. Liquid hydrophillic polymer solution is added to the tub in an amount adequate to form a bath and pan coat a brush. Brush is added to bath and allowed to sit for 30 seconds. It is also possible to simply run a spool of brush material through a bath using a manufacturing system, or alternatively use a conventional spray apparatus to apply the hydrophilic polymer to the brush. When the coating process is completed, the brush is cured. After the coating cures, a detergent rinse may be added to clean the coating layer. Brush is dried at an elevated temperature. Preferably the brush is dried at between 27 and 38° C. Most preferably brush is dried at 32.2° C. Coated brush is next cooled by supplying dry air of about room temperature for about 10 to 20 minutes. Brush coated with a hydrophilic polymer may then be further coated with cleaning solution, such as those described above, including non-ionic detergent, disinfectant, or an enzyme-based cleaning composition. Disinfectant may further be added to the coating layer. Other preferred embodiments using a leader require the step of fixing a leader of predetermined length and diameter to a brush of predetermined length and diameter. Preferably a leader is attached to brush by placing a 1 ml. of bonding resin such as Krazy Glue® to the first end of the brush, and fixing the second end of the leader to the first end of the brush.

Figure 6A:
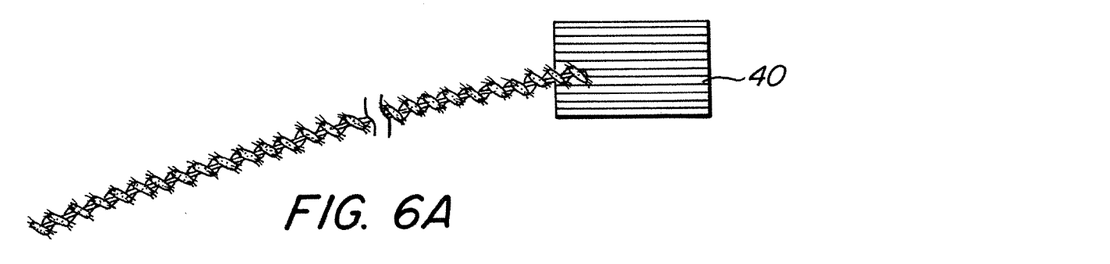
FIGS. 6(A)-6(D) are side views of a brush as shown in FIGS. 1, 2A and 2B showing the bristle portion in representative form.
Figure 6B:
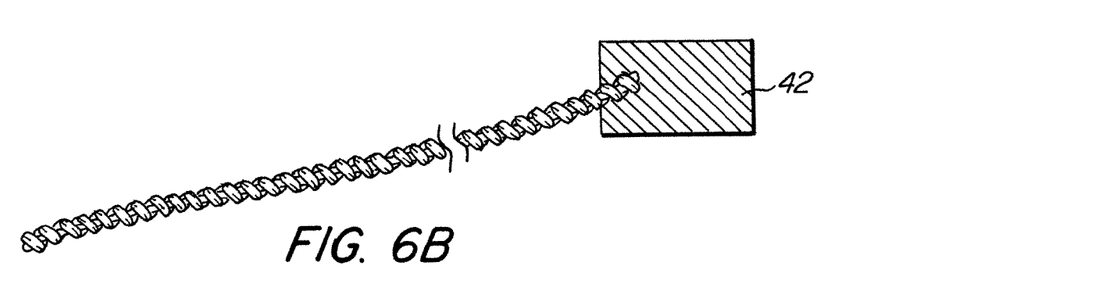
Figure 6C:
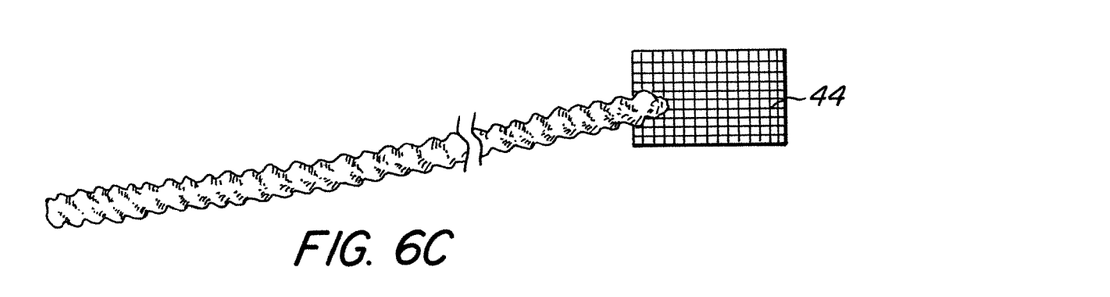
Figure 6D:
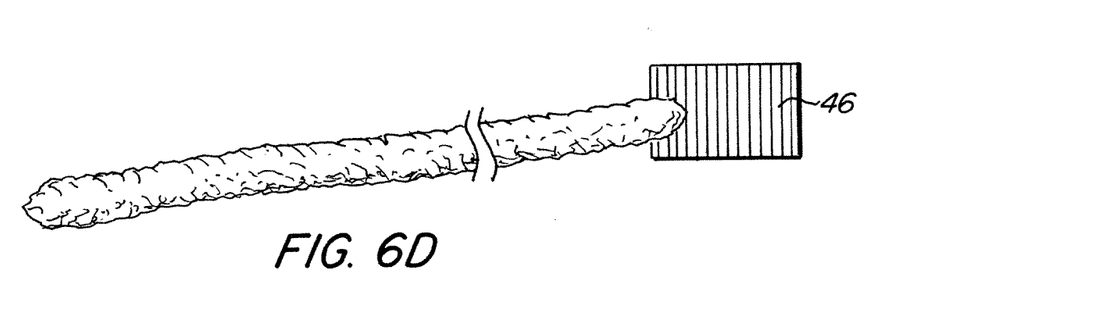

Other embodiments of the present invention include color-coded bristle portions of brush to aid the user in selecting the desired diameter brush portion. It is well known that lumens have a variety of known diameters. Brushes of the present invention are preferably pre-sized before use so that the brush portion diameter is about equal to the diameter of the lumen. The diameter of the brush portion is preferably slightly larger than the diameter of the lumen. Compressible bristles allow brush to easily fit into lumen. Color-coding brush portions aids non-technical persons in sizing the appropriate brush by simply matching a known brush color with a lumen of known dimensions. Referring back to the drawings, FIG. 6A shows a blue (40) brush having a bristle portion of a first predetermined diameter. Preferably, the first predetermined diameter is about 1.5 mm. FIG. 6B shows a green (42) brush having a bristle portion of a second predetermined diameter. Preferably, the second predetermined diameter is about 2.5 mm. FIG. 6C shows a yellow (44) brush having a bristle portion of a third predetermined diameter. Preferably, the third predetermined diameter is about 4.0 mm. FIG. 6D shows a red (46) brush having a bristle portion of a fourth predetermined diameter. Preferably, the fourth predetermined diameter is about 6.0 mm. It should be understood that any color may be associated with any known diameter size and that FIGS. 6A-6D are illustrative and not limiting and that obvious modifications may be made by those skilled in the art without departing from the spirit of the invention.

Figure 7:
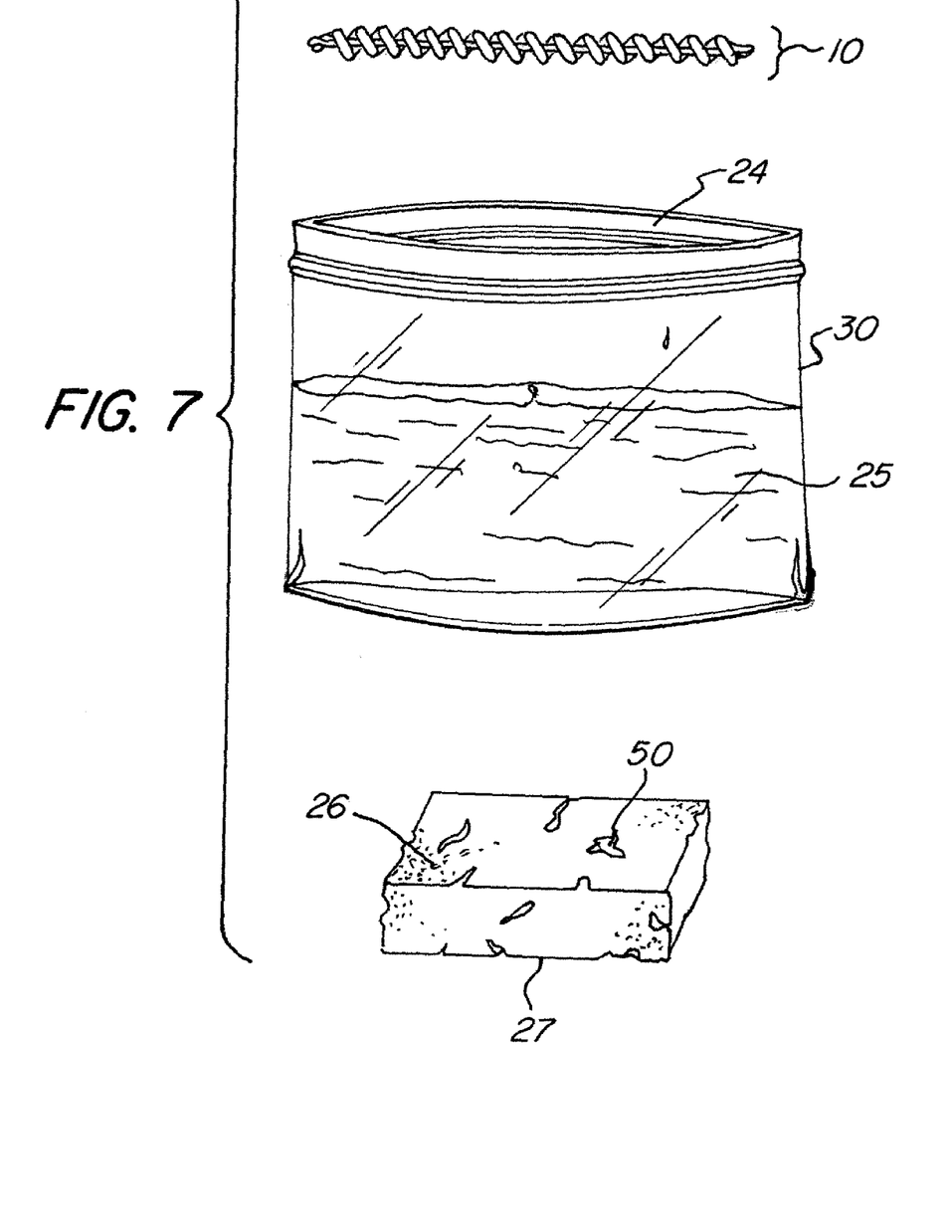
FIG. 7 is a side view of a kit including a brush as shown in FIGS. 1, 2A and 2B showing a kit in representative form.

FIG. 7 shows a kit embodiment of the present invention. A kit for cleaning a soiled lumen having brush 10 of the present invention; a pouch 30 having an inner space 24 for holding liquid cleaning solution 25; a liquid cleaning solution 25; and/or a hand pad 26 having an outer surface 27. Liquid cleaning solution 25 may be a water-based buffer containing anti-microbial agents, and/or a water-based buffer containing detergents suitable for cleaning soiled surgical instruments, and/or a water-based enzyme cocktail. Inner space 24 is of a predetermined volume capable of holding between 10 to 500 ml of liquid cleaning solution, preferably about 75 ml. Hand pad 26 may be shaped to accommodate a lumen within the hand pad. Hand pad may have pores 50. Hand pad 27 may be made out of any sponge, or foam material suitable for wiping objects, such as natural sponge. Hand pad 27 may be flat. Preferably hand pad 27 is 3.5"×5.5"×3⁄8" to 5⁄8". Hand pad 27 may be die cut so it conforms to the scope.

FIG. 10 shows a side view of cleaning element of the present invention. Brush 10 is comprised of a bristle portion 7, which is further comprised of bristles 6. Brush 10 is further shown having core 1, and a substantially longitudinal axis 4 extending throughout the length of brush 10. Preferably, brush portion 7 is 6 inches or longer. Leader 5 is shown attached directly to core 1 at first end of brush portion 2. Attaching leader 5 directly to core 1 of brush 10 facilitates the passage of cleaning element into a lumen or surgical instrument. Moreover, attaching leader 5 directly to core 1 may make cleaning element more durable. Leader 5 may be a wire and attached to core 1 by known soldering techniques, or any other method of joining substantially blunt ends.

Figure 11:
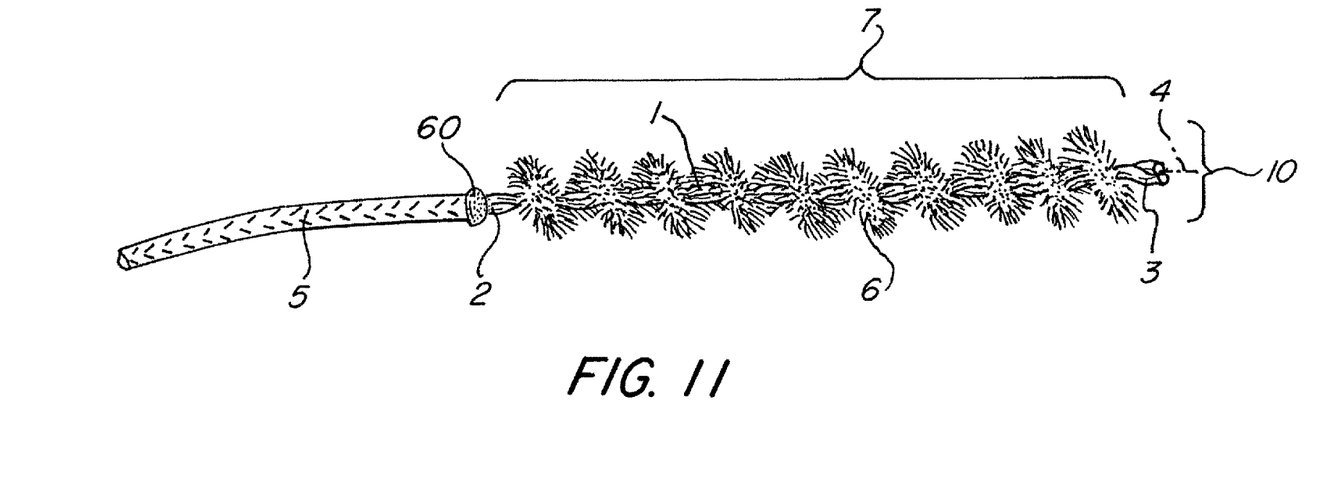
FIG. 11 is a side view of a brush with leader in accordance with another embodiment of the present invention.

FIG. 11 shows a side view of cleaning element of the present invention, and is similar to the cleaning element shown in FIG. 10. In the cleaning element shown in FIG. 11, however, both leader 5 and core 1 of brush portion 7 are formed from a metal material. Leader 5 may be made out of metal wire, twisted metal wire segments, or the like, and may be made from any metal materials that are already well known in the art, e.g., a conventional soft steel or iron wire, or that may be later developed. It has been found that forming leader from a stainless steel braided wire provides acceptable results. Core 1 of brush portion 7 may be configured as discussed above in connection with FIG. 5, and may be formed from any metal materials that are already well known in the art, e.g., a conventional soft steel or iron wire, or that may be later developed. Leader 5 and core 1 are welded together so as to create a high strength bond therebetween. Any of numerous welding techniques, such as spot welding, arc welding, oxy-acetylene welding, electron beam welding, plasma beam welding, cold-press welding, friction welding, ultrasonic metal welding, etc. may be used to create weld 60 between leader 5 and core 1 of brush portion 7. By forming both leader 5 and core 1 of brush portion 7 of a metal material and welding leader 5 and core 1 together, it is virtually guaranteed that brush portion 7 will not unintentionally become detached from leader 5 during normal use of the cleaning element.

Figure 12A:
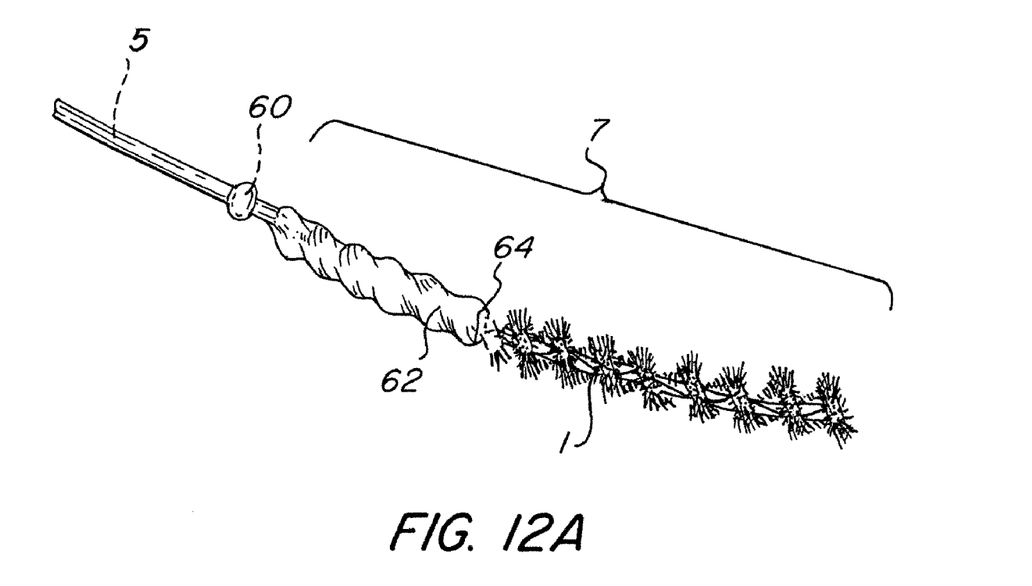
FIGS. 12A and 12B are side views of the brush with leader of FIG. 11 in which the leader is covered by a jacket.
Figure 12B:
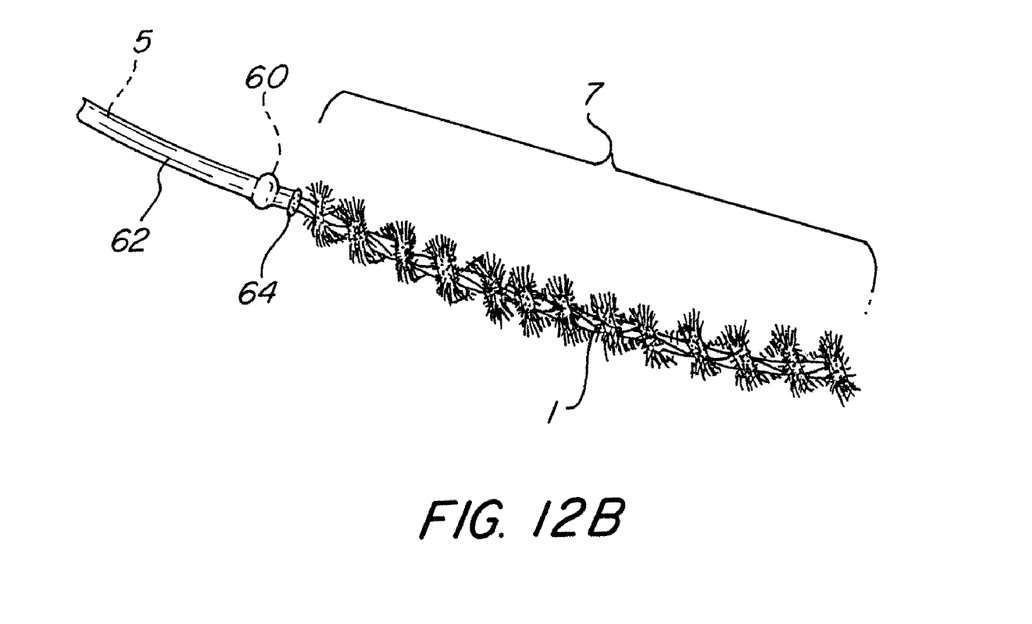

While it is possible to form leader 5 and weld 60 such that they have smooth outer surfaces, thereby reducing the likelihood of damage to the lumen of the surgical instrument during cleaning thereof, and some embodiments are formed in this fashion without any additional coating (such as the embodiment shown in FIG. 11), in other embodiments, such as those shown in FIGS. 12A and 12B, a jacket or coating 62 may be provided over leader 5 and/or weld 60. By providing jacket or coating 62, it is not required for leader 5 and/or weld 60 to have smooth outer surfaces, since jacket or coating 62, having a smooth outer surface itself, is what contacts the lumen of the surgical instrument during cleaning thereof. The jacket or coating 62 may cover a portion of the brush portion 7 (as shown in FIG. 12A) and have an end 64 terminating within brush portion 7, which may aid in retaining jacket or coating 62 on leader 5 without slipping off during use, or jacket or coating 62 may have an end 64 terminating before brush portion 7 (as shown in FIG. 12B), such that substantially all of brush portion 7 is exposed. Jacket or coating 62 may be formed from any of numerous materials, although it has been found that polymer materials, particularly nylon, provide desirable results.

Cleaning elements and kits of the present invention provide the following benefits:

Removing and dissolving, blood, fat, proteins, mucous and other organic contaminates from soiled surgical instruments and lumens.

Maintaining contact and positive pressure between enzyme and lumen during soaking cycle.

Full-length cylindrical bristle portion of brush effectively removes residual debris from interior of soiled lumens or surgical instruments.

Decrease time required to clean surgical instruments.

Does not damage instrument seals or rings.

Prevents corrosion of stainless steel and carbon steel surgical instruments.

Increases the effectiveness of the enzyme/surfactant cleaning properties.

Increases effectiveness of decontamination and sterilization of precleaned surgical instruments.

It should be understood that the invention has been described for use with cleaning elements for the sake of convenience only and is not intended to be limiting. Other articles may be made in a similar manner after reading and understanding this disclosure.

It should also be understood that the foregoing is illustrative and not limiting and that obvious modifications may be made by those skilled in the art without departing from the spirit of the invention. Accordingly, reference should be made primarily to the accompanying claims, rather than the foregoing specification, to determine the scope of the invention.

What is claimed is:

1. A cleaning element for lumen of surgical instruments comprising:
a brush having a plurality of bristles, a first end, a second end, and a metal core, the metal core defining a longitudinal axis extending throughout said brush;
a metal leader having a first end and a second end, the second end of said metal leader being welded to the first end of the metal core of said brush;
a weld where said leader is welded to said core, and a jacket or coating covering said metal leader and said weld between said metal leader and the metal core of said brush;
wherein the jacket or coating has a first end covering a portion of the bristles of said brush and has a second end terminating in an area adjacent to the bristles of said brush; and
wherein said metal leader is adapted to be fed through the lumen of the surgical instruments and pulled by the first end thereof through the lumen, with said brush also being adapted to be threaded through the lumen due to its being welded to the second end of said metal leader.

2. The cleaning element of claim 1 wherein said metal leader comprises metal wire or twisted metal wire segments.

3. The cleaning element of claim 2 wherein said metal leader is formed from steel or iron.

4. The cleaning element of claim 3 wherein said metal leader comprises stainless steel braided wire.

5. The cleaning element of claim 1 wherein the metal core of said brush comprises a pair of twisted metal wire segments.

6. The cleaning element of claim 5 wherein the plurality of bristles secured between the pair of twisted wire segments.

7. The cleaning element of claim 1 wherein the second end of said metal leader is attached to the first end of the metal core of said brush by a weld made with at least one of the following welding techniques: spot welding, arc welding, oxy-acetylene welding, electron beam welding, plasma beam welding, cold-press welding, friction welding, and ultrasonic metal welding.

8. The cleaning element of claim 1 wherein the jacket or coating is formed from a polymer material.

9. The cleaning element of claim 8 wherein the jacket or coating is formed from nylon.

10. A cleaning element for lumen of surgical instruments comprising:
a brush having a first end, a second end, and a metal core, the metal core defining a longitudinal axis extending throughout said brush;
a metal leader having a first end and a second end, the second end of said metal leader being welded to the first end of the metal core of said brush; and
a weld where said leader is welded to said core, and a jacket or coating covering said metal leader and said weld between said metal leader and the metal core of said brush; and
wherein said brush further comprises a plurality of bristles, and wherein the jacket or coating has a first end covering a portion of the bristles of said brush and has a second end terminating in an area adjacent to the bristles of said brush.

11. The cleaning element of claim 10 wherein the jacket or coating is formed from a polymer material.

12. The cleaning element of claim 11 wherein the jacket or coating is formed from nylon.

13. The cleaning element of claim 10 wherein said metal leader is adapted to be threaded through the lumen of the surgical instruments and pulled by the first end thereof through the lumen, with said brush also being adapted to be pulled through the lumen due to its being welded to the second end of said metal leader.

14. The cleaning element of claim 10 wherein said metal leader comprises metal wire or twisted metal wire segments.

15. The cleaning element of claim 14 wherein said metal leader is formed from steel or iron.

16. The cleaning element of claim 15 wherein said metal leader comprises stainless steel braided wire.

17. The cleaning element of claim 10 wherein the metal core of said brush comprises a pair of twisted metal wire segments.

18. The cleaning element of claim 17 wherein said brush further comprises a plurality of bristles secured between the pair of twisted wire segments.

19. The cleaning element of claim 10 wherein the second end of said metal leader is welded to the first end of the metal core of said brush by at least one of the following welding techniques: spot welding, arc welding, oxy-acetylene welding, electron beam welding, plasma beam welding, cold-press welding, friction welding, and ultrasonic metal welding.

20. A kit for cleaning a soiled lumen having a first end and a second end comprising:
the cleaning element of claim 1;
a pouch having an inner space for holding liquid solution; and
a liquid cleaning solution.

21. A kit for cleaning a soiled lumen having a first end and a second end comprising:
the cleaning element of claim 10;
a pouch having an inner space for holding liquid solution; and
a liquid cleaning solution.

* * * * *